United States Patent
Forkner (10) Patent No.: US 8,143,461 B2
(45) Date of Patent: Mar. 27, 2012

(54) MALEIC ANHYDRIDE CATALYST AND METHOD FOR ITS PREPARATION

(75) Inventor: Matthew W. Forkner, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 474 days.

(21) Appl. No.: 12/439,035

(22) PCT Filed: Aug. 24, 2007

(86) PCT No.: PCT/US2007/076747
§ 371 (c)(1),
(2), (4) Date: Feb. 26, 2009

(87) PCT Pub. No.: WO2008/030714
PCT Pub. Date: Mar. 13, 2008

(65) Prior Publication Data
US 2010/0016644 A1 Jan. 21, 2010

Related U.S. Application Data (60) Provisional application No. 60/824,529, filed on Sep. 5, 2006.

(51) Int. Cl.
*C07C 27/10* (2006.01)
*C07D 307/36* (2006.01)
*B01J 27/198* (2006.01)

(52) U.S. Cl. .......................... 568/956; 549/262; 502/209
(58) Field of Classification Search ................... 568/956; 549/262; 502/209
See application file for complete search history.

(56) References Cited

U.S. PATENT DOCUMENTS

| | | | |
|---|---|---|---|
| 4,043,943 A | 8/1977 | Schneider |
| 5,137,860 A | 8/1992 | Ebner et al. |
| 5,275,996 A | 1/1994 | Andrews et al. |
| 5,364,824 A | 11/1994 | Andrews et al. |
| 5,401,707 A | 3/1995 | Benziger et al. |
| 5,480,853 A | 1/1996 | Bortinger |
| 5,773,382 A | 6/1998 | Mitchell et al. |
| 5,792,722 A | 8/1998 | Haddad et al. |
| 5,922,637 A | 7/1999 | Bortinger |
| 6,046,343 A | 4/2000 | Mummey et al. |
| 6,107,234 A | 8/2000 | Bortinger |
| 6,174,833 B1 | 1/2001 | Bertola et al. |
| 6,660,681 B1 | 12/2003 | Ledoux et al. |
| 6,762,146 B2 | 7/2004 | Kamiya et al. |
| 6,774,081 B1 | 8/2004 | Datta et al. |
| 6,858,561 B2 | 2/2005 | Bortinger et al. |
| 6,903,047 B2 | 6/2005 | Kourtakis et al. |
| 6,956,004 B2 | 10/2005 | Albonetti et al. |

*Primary Examiner* — Sikarl Witherspoon
(74) *Attorney, Agent, or Firm* — Huntsman Petrochemical LLC (57) ABSTRACT

The present invention provides a process for producing a vanadium/phosphorus oxide catalyst by (i) preparing a catalyst precursor powder containing vanadium, phosphorus and an optional promoter element; (ii) converting the catalyst precursor powder into an activated catalyst by heat treatment; (iii) and compressing the activated catalyst into a desired shape to form the vanadium/phosphorus oxide catalyst. The vanadium/phosphorus oxide catalyst may be used in the production of maleic anhydride by the catalytic oxidation of hydrocarbon feed streams.

12 Claims, 3 Drawing Sheets

FIG. 3

MALEIC ANHYDRIDE CATALYST AND METHOD FOR ITS PREPARATION

CROSS-REFERENCE TO RELATED APPLICATIONS

This application is the National Phase of International Application PCT/US2007/076747 filed Aug. 24, 2007 which designated the U.S. and which claims priority to U.S. Provisional App. Ser. No. 60/824,529 filed Sep. 5, 2006. The noted applications are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention is directed to a vanadium/phosphorus oxide catalyst, method of preparation of such catalyst, and the use of the catalyst in the production of maleic anhydride.

2. Background of the Invention

Maleic anhydride may be used as a raw material in the production of many products, such as synthetic resins, and may generally be prepared by the catalytic oxidation of n-butane. The catalyst of choice for this oxidation is typically a catalyst containing vanadium, phosphorus, oxygen (VPO), and optionally a promoter component.

These VPO catalysts are generally prepared by contacting vanadium-containing compounds with phosphorus-containing compounds and optionally promoter component containing-compounds under conditions suitable to reduce the pentavalent vanadium to the tetravalent state to thereby form a catalyst precursor containing vanadyl hydrogen phosphate and optionally the promoter component. The catalyst precursor may then be recovered and typically formed into a shaped body, such as a tablet or pellet, by compression in a die. A lubricant is ordinarily incorporated as well to aid in the tableting or pelleting process. The pellet or tablet may then be subjected to calcination to transform the catalyst precursor into an active catalyst containing vanadyl pyrophosphate.

In addition to promoter components, VPO catalysts may be prepared by further adding high vapor pressure additives to control the pore structure of the catalyst as disclosed in U.S. Pat. No. 5,275,996, which is incorporated by reference herein in its entirety. Additives disclosed in this reference include polyethylene oxide, adipic acid, citric acid, oxalic acid, stearic acid, palmitic acid, lauric acid, myristic acid, esters of such acids, naphthalene, polyethylene glycol, polyvinyl alcohol, polyacrylic acid, cellulosic materials, monosaccharides, polysaccharides, hydrogenated vegetable oils, waxes, and gelatin. One drawback to the use of these additives is that the additives are removed from the catalyst by heat treatment at elevated temperatures, typically with the use of a stripping gas, which can deactivate the catalyst, cause overstripping or dehydration and reduce productivity of the catalyst due to increased processing time and rigorous control needed in handling a flammable material at elevated temperatures.

Thus, efforts are continually being made to define new and improved VPO catalysts and methods and processes of making new and old VPO catalysts in order to reduce cost and/or upgrade the activity, selectivity, and productivity of such catalysts.

BRIEF SUMMARY OF SOME OF THE PREFERRED EMBODIMENTS

These and other needs in the art are addressed in one embodiment by a process for producing vanadium/phosphorus oxide catalysts, which are useful for the oxidation of nonaromatic hydrocarbons to produce maleic anhydride. The process includes the steps of preparing a catalyst precursor powder by mixing a vanadium compound with a phosphorus compound in a medium comprising alcohol and drying the mixture, forming the catalyst precursor powder into catalyst precursor slugs under compression, converting the catalyst precursor slugs into an activated catalyst by heat treatment, and forming the activated catalyst into a predetermined shape under compression to produce the vanadium/phosphorus oxide catalyst. The activated catalyst may also be treated with a solvent-removable pore building agent prior to forming into the predetermined shape to provide a vanadium/phosphorus oxide catalyst containing a high concentration of pores therein for rapid internal and external diffusion of product and reactant gases within the oxide catalyst.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

An embodiment includes a process for preparing a vanadium/phosphorus oxide catalyst effective in the catalytic oxidation of hydrocarbons, more particularly, the catalytic oxidation of $C_4$ hydrocarbons to maleic anhydride. It has been surprisingly discovered that enhanced activity and productivity in the conversion of n-butane or other hydrocarbons to maleic anhydride may be achieved when using the catalyst prepared by the process. In addition, the vanadium/phosphorous oxide catalyst may exhibit better uniformity in its final chemical properties as compared to catalysts produced by traditional methods.

The vanadium/phosphorus oxide catalyst comprises shaped bodies having a B.E.T. surface area of at least about 15 $m^2/g$, an average vanadium oxidation state from about 4.0 to about 4.5, a total pore volume of at least about 0.15 $cm^3/g$, a normalized apparent shaped body density of between about 1.0 and about 2.0 g/cm, a crush strength of at least about 4 pounds, and a phosphorous:vanadium atomic ratio from about 1.0 to about 1.2. The catalysts may be prepared by a process that includes activating a catalyst precursor to produce an activated catalyst, optionally treating the activated catalyst with a solvent-removable pore building agent, forming the activated catalyst into a predetermined shape, removing the optional pore building agent from the shaped catalyst with the appropriate solvent and drying at moderate temperatures to produce the vanadium/phosphorus oxide catalyst.

For purposes of this invention, the term "yield" means the ratio of the moles of maleic anhydride obtained to the moles of hydrocarbon feedstock introduced into the reactor multiplied by 100 with the term expressed as mole percent.

The term "selectivity" means the ratio of the moles of maleic anhydride obtained to the moles of hydrocarbon feedstock reacted or converted multiplied by 100 with the term expressed as mole percent.

The term "conversion" means the ratio of the moles of hydrocarbon feedstock reacted to the moles of hydrocarbon feedstock introduced into the reactor multiplied by 100 with the term expressed as mole percent.

The term "weight/weight productivity" means the weight of maleic anhydride produced per unit of catalyst per hour.

The term "weight/area productive" means the weight of maleic anhydride produced per unit B.E.T. developed surface area of catalyst per hour.

The term "space velocity" or "gas hourly space velocity" or "GHSV" means the volumetric flow rate of gaseous feed expressed in standard (273K, 14.7 psig) cubic centimeters per hour divided by the bulk catalyst volume expressed in cubic centimeters with the term expressed as $cm^3/cm^3/hour$ or $hr^{-1}$.

The term "gas flow volume to catalyst weight ratio" means the ratio of the volumetric flow rate of gas containing a hydrocarbon and air or oxygen to the weight of a catalyst bed through which the gas is flowing with the term expressed in g/cc-min.

Catalyst precursors suitable for use may be prepared according to those described in U.S. Pat. Nos. 5,137,860 and 5,364,824, which are each incorporated by reference herein in their entirety. In general, the catalyst precursors are represented by the formula:

$$VO(M)_m HPO_4 \cdot aH_2O \cdot b(P_{2/c}O) \cdot n(\text{organics})$$

where M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof; m is a number from zero (0) to about 0.2; a is a number of at least about 0.5; b is a number taken to provide a P/V atom ratio from about 0.9 to about 1.3; c is a number representing the oxidation number of phosphorus and has a value of 5; and n is a number taken to represent the weight % of intercalated or occluded organics component.

The catalyst precursor may be prepared by introducing a substantially pentavalent vanadium-containing compound and a pentavalent phosphorus-containing compound into an alcohol medium to form a catalyst precursor slurry. The vanadium and phosphorus-containing compounds may be added simultaneously, or one after the other, in any convenient manner to the alcohol medium. After the vanadium and phosphorus-containing compounds are introduced into the alcohol medium to form the catalyst precursor slurry, reduction of at least a portion of the vanadium to a valence state of +4 is effected, preferably by heating the mixture, with stirring, if desired, until a blue solution or slurry is obtained. In general, heating the slurry at the reflux temperature for a period of time ranging from about four (4) hours to about twenty (20) hours is sufficient.

The pentavalent vanadium-containing compounds that may be used as a source of vanadium in the vanadium/phosphorous oxide catalysts include vanadium pentoxide or vanadium salts, such as ammonium metavanadate, vanadium oxytrihalides, and vanadium alkylcarboxylates. Among these compounds, vanadium pentoxide is preferred.

The pentavalent phosphorus-containing compounds useful as a source of phosphorus in the vanadium/phosphorous oxide catalysts include phosphoric acid, phosphorus pentoxide, or phosphorus perhalides such as phosphorus pentachloride. Of these phosphorus compounds, phosphoric acid and phosphorus pentoxide are preferred.

The alcohols employed in the preparation of the catalyst precursor are preferably anhydrous and, in some embodiments, capable of reducing at least a portion of the vanadium to a +4 valence state, either upon addition of the vanadium compound or upon mixing and heating. In addition, the alcohol may be a solvent for and relatively unreactive toward the phosphorus compound. Preferably, the alcohol is not a solvent for the catalyst precursor. In those instances where the catalyst precursor is soluble in the alcohol medium, precursor precipitation may be easily induced by removal of a portion of the alcohol. Suitable alcohols include primary and secondary alcohols, such as methanol, ethanol, 1-propanol, 2-propanol, 1-butanol, 2-methyl-1-propanol (isobutyl alcohol), 2-butanol, 3-methyl-2-butanol, 2,2-dimethyl-1-propanol, 4-methyl-2-pentanol, and 1,2-ethanediol (ethylene glycol). Of these alcohols, isobutyl alcohol (IBA) is preferred.

If desired, optional promoter elements may be added as solids, suspension of solids, or solutions to the catalyst precursor slurry. Promoter compounds that may serve as sources of the promoter elements include metal halides, metal alkoxides, and metal carboxylates. Of these compounds, metal carboxylates are preferred. Suitable carboxylates for metal salts include formate, acetate, propionate, butyrate, isobutyrate, penitanoate, hexanoate, heptanoate, octanoate, nonanoate, decanoate, and 2-ethylhexanoate. Of these carboxylates, 2-ethylhexanoate is preferred. In an embodiment, the promoter elements comprise Mo, Nb, Cr, Fe, or combination thereof.

The promoter elements may be added to the catalyst precursor slurry as metal 2-ethylhexanoates in solutions of alcohols, esters, aromatics, and alkanes. Of these solvents, isobutyl alcohol, isobutyl isobutyrate, decane, and mineral spirits constitute preferred but not limiting solvents of choice. In an embodiment, the metal 2-ethylhexanoates are dissolved in suitable solvents in amounts of 20 percent by weight or less before they are added to the slurry.

The promoter metal 2-ethylhexanoates may be added to the vanadium-phosphorus oxide catalyst precursor slurry before, during, or after the reflux period at slurry temperatures ranging from ambient to the reflux temperature of the catalyst precursor slurry mixture. Of these times of addition, during the reflux period is preferred and at a slurry temperature of less than 40° C. Because the promoter source is generally reactive with the phosphorus compound, it is preferably withheld from the reaction system until the vanadium compound has been substantially consumed by reaction to a VPO compound. Otherwise, in some embodiments, the P/V ratio may be increased to above the optimum. Without being limited by theory, such increase is for the purpose of driving the reaction of the vanadium compound to completion. One method of preparation, therefore, is referred to as the "post" method, in which the vanadium compound is first reacted at elevated temperature with a modest excess of phosphorus compound, for example, at a P/V ratio of 1.05 to 1.20, until the vanadium compound is substantially exhausted; and thereafter the promoter source compound is reacted with the residual phosphorus compound to incorporate the promoter in the catalyst precursor. The reaction between the vanadium and phosphorus compounds may be carried out at any suitable temperature. In an embodiment, the reaction may be carried out at a temperature in the range of between about 90° and about 120° C., conveniently at atmospheric reflux temperature. The reaction mixture may then be cooled to below 40° C. for addition of the promoter source.

In another embodiment, the vanadium compound and phosphorus compound are reacted at a temperature in the range of between about 90° C. and about 120° C., again using a P/V ratio of 1.05 to 1.15; the reaction mixture is cooled below 40° C. for addition of the promoter source, and optionally a further increment of phosphoric acid; and then the reaction system is again heated to a temperature in the range of between about 90° C. and about 120° C. for incorporation of the promoter compound into the precursor structure.

During the course of carrying out the vanadium reduction, the catalyst precursor forms and precipitates from the alcohol medium as a finely divided precipitate that contains the optional promoter elements. The catalyst precursor precipitate may be recovered after cooling to below about 50° C. by conventional techniques well known to those skilled in the art, including filtration, centrifugation, and decantation. The resulting catalyst precursor powder after drying has a powdery, free-flowing consistency in contrast to a caked residue normally obtained when the catalyst precursor is recovered by heating the solution to dryness.

To avoid reaction of the alcohol with catalytically active vanadium sites, the drying may be performed in an atmosphere of low or no oxygen content such as dry nitrogen. The catalyst precursor precipitate may be dried at a relatively modest temperature of, for example, about 110° C. to about 150° C., and then subjected to "post dry" treatment (roasting) at a temperature in the range of about 200° C. to about 275° C. In one embodiment the post dry treatment is carried out by fluidizing the catalyst precursor powder in an inert gas in the post dry temperature range. Once the bed reaches the desired temperature, it may be held at that temperature for a suitable period, for example 30 minutes to two hours, and thereafter an air/steam mixture is introduced, preferably on an incremental schedule to a maximum of about 10 to about 30% oxygen, after which the bed is cooled in an inert atmosplere to room temperature.

Although the catalyst precursor powder that is obtained may be directly converted to an activated catalyst by the gas and thermal treatments described below, a preferred embodiment includes that the catalyst precursor powder first be compressed in a press or die to produce a catalyst precursor slug. The slug may be compressed into any desired shape or form, such as a cylinder, cube, or sphere, to a measured density of between about 1.20 g/cm$^3$ to about 1.70 g/cm$^3$, preferably between about 1.40 g/cm$^3$ to about 1.60 g/cm$^3$. The catalyst precursor slug may have a minimum principal dimension of at least about 1/16 inch to about 1/8 inch, preferably at least about 5/32 inch to about 1/2 inch. Binding and/or lubricating agents may be added if desired at amounts ranging from about 2 to about 6%, alternatively from about 0 to about 10%, and alternatively from about 2 to about 6% by weight based on the total veiglht of the precursor slug and may include starch, calcium stearate, stearic acid and graphite.

The catalyst precursor powder or slugs may then be converted into an activated catalyst by a series of steps in a controlled manner using a sequence of gas and thermal treatments, sometimes referred to as calcination. Without being limited by theory, such conversion is preferred for the preparation of superior catalysts. This conversion may be accomplished in three controlled stages: (1) an initial heat-up stage, (2) a rapid heat-up stage, and (3) a maintenance/finishing stage.

In one embodiment, the catalyst precursor slug is heat treated in the three stages to produce the activated catalyst as described in U.S. Pat. No. 5,137,860 which is incorporated herein by reference in its entirety. The activated catalyst produced by activation corresponds to a composition represented by the formula:

$$(VO)_2(M)_m P_2 O_7 \cdot b(P_{2/c} O)$$

where M is at least one promoter element selected from among elements of Groups IA, IB, IIA, IIB, IIIA, IIIB, IVA, IVB, VA, VB, VIA, VIB, and VIIIA of the Periodic Table of the Elements, and mixtures thereof; m is a number from zero (0) to about 0.2; b is a number taken to provide a P/V atom ratio from about 1.0 to about 1.3; and c is a number representing the oxidation number of phosphorus and has a value of 5. The oxidation state of the vanadium is between about 4.0 and about 4.5, preferably between about 4.06 and about 4.30.

Although the activated catalyst, as represented by the above formula, is indicated as having a phosphorus-to-vanadium (phosphorus/vanadium or P/V) atom ratio from about 1.0 to about 1.3, preferably from about 1.0 to about 1.2, most preferably from about 1.05 to about 1.15, the actual P/V atom ratio may range from a value as low as about 0.9 up to the stated value of about 1.3. The total atom ratio of promoter element-to-vanadium (promoter element/vanadium or M/V), when a promoter element is present as a component of the activated catalyst, may be in the range from about 0.0001 to about 0.2, preferably from about 0.0005 to about 0.1, most preferably from about 0.001 to about 0.05. The activated catalyst may exhibit enhanced catalyst activity and excellent selectivities to and yields of maleic anhydride. Further enhancement of activity may be provided by the use of a solvent-removable pore modification agent to produce high fractions of pores within the catalyst as described below.

In the initial heat-up stage, the catalyst precursor slug may be heated in an atmosphere selected from among air, steam, inert gas, and mixtures thereof, at any convenient heat-up rate. In an embodiment, the catalyst precursor slug may be heated to a temperature not to exceed the phase transformation initiation temperature, which may be about 300° C. In general, suitable temperatures for the initial heat-up stage range from about 200° to about 300° C., alternatively a temperature from about 250° to about 275° C.

After the desired temperature has been achieved in the initial heat-up stage, the initially selected atmosphere (in the event it does not contain molecular oxygen and steam and/or has a different composition than that which is desired for the rapid heat-up stage) may be replaced by a molecular oxygen/steam-containing atmosphere, while maintaining the catalyst precursor at the temperature achieved in the initial heat-up stage. Such atmosphere optionally may contain an inert gas and, as such, may be conveniently represented by the formula:

$$(O_2)_x (H_2O)_y (IG)_z$$

where IG is an inert gas and x, y, and z represent mole % (or volume %) of the $O_2$, $H_2O$, and IG components, respectively, in the molecular oxygen/steam-containing atmosphere; with x having a value greater than zero (0) mol %, but less than 100 mol %; y having a value greater than zero (0) mol %, but less than 100 mol %; and z having a value representing the balance of the molecular oxygen/steam-containing atmosphere. In an embodiment, the atmosphere may contain at least a portion of molecular oxygen and water (as steam). The presence of the inert gas in such atmosphere, as indicated by the formula, is optional. Nonlimiting examples of inert gases suitable for use in the molecular oxygen/steam-containing atmosphere include (molecular) nitrogen, helium, argon, and the like, with nitrogen generally being preferred.

Once the molecular oxygen/steam-containing atmosphere is provided, the catalyst precursor slug may be subjected to the rapid heat-up stage. In the rapid heat-up stage, the initial heat-up stage temperature is increased at a programmed rate of from about 2° C. per minute (° C./min) to about 12° C./min, preferably from about 4° C./min to about 8° C./min, to a value effective to eliminate or remove the water of hydration from the catalyst precursor slug. In general, a temperature from about 340° C. to about 450° C., alternatively at least about 350° C., alternatively from about 375° C. to about 425° C. is suitable.

Following the rapid heat-up stage, the catalyst precursor may be subjected to the maintenance/finishing stage. In the maintenance/finishing stage, while the molecular oxygen/steam-containing atmosphere, is maintained, the temperature may be adjusted to a value greater than 350° C. but less than 550° C., preferably from about 375° C. to about 450° C. most preferably from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a non-oxidizing, steam-containing atmosphere for a time effective to complete the catalyst precursor-to-active catalyst transformation to yield the activated catalyst. In a manner similar to the molecular oxygen/steam-containing atmosphere, the non-oxidizing, steam-containing atmosphere may also optionally contain an inert gas, with nitrogen generally being the preferred inert gas.

It is to be understood that the nonoxidizing, steam-containing atmosphere need not necessarily be completely free of molecular oxygen. However, in an embodiment, such atmosphere preferably is substantially free of molecular oxygen. Accordingly, molecular oxygen may be present in an amount that is not effective to cause further oxidation of the vanadium beyond the desired oxidation state of about +4.0 to about +4.5, more particularly, not beyond the maximum desired oxidation state of about +4.5. In general, molecular oxygen may be present in amounts that do not exceed about 0.5 mol % of the nonoxidizing, steam-containing atmosphere.

The period of time during which the adjusted temperature is maintained in the molecular oxygen/steam-containing atmosphere in order to provide the desired vanadium oxidation state of from about +4.0 to about +4.5 may depend to some extent upon the vanadium oxidation state achieved during the rapid heat-up stage, which, in turn, may depend to some extent upon the period of time during which the catalyst precursor is exposed to the molecular oxygen/steam-containing atmosphere at the stated rapid heat-up stage temperatures. In an embodiment, a period of time of from about 0.25 hours to about 2 hours is suitable, with a period of time of from about 0.5 hour to about 1 hour being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

The activated catalyst may then be granulated, optionally treated with a solvent-removable pore agent, and further compressed in a press or die into a predetermined shape to produce the shaped body catalyst. Granulation of the activated catalyst into granules may be carried out by the mechanical action of mill knives operated in conjunction with a retaining screen having holes which pass the desired the size granule. In one embodiment, the granules are on the order of 200 μm to 1 mm in size, as produced by passage through a screen having 1/16" to 1/8" holes.

The granules may then be optionally mixed with a solvent-removable pore building agent. A substantial volume of pores within the catalyst may be obtained through the use of the solvent-removable pore building agent. In addition, since mild conditions are employed in generating the pores, the desired pore size distribution may be realized without adversely affecting the activity at the active internal surfaces of the catalyst.

The solvent-removable pore building agent may be added to the granules so that the mixture contains between about 6% and about 16%, preferably between about 8% and about 12% by weight of pore building agent based on the total weight of the granules.

The solvent-removable pore building agent that may be added includes a carboxylic acid, anhydride, ester, alcohols, polyols, carbohydrates, ketones, waxes, aromatic hydrocarbons (e.g., naphthalene), polymers (e.g., polystyrene, polyvinyl alcohol (PVA)), or combination thereof. In an embodiment, the pore agent is a solid at the temperatures typically found during compaction and tableting and does not negatively chemically interact with the vanadium phosphate catalyst.

In one embodiment, the solvent-removable pore building agent is 1,1,1-tris(hydroxymethyl)ethane, trimethyolpropane, maleic anhydride, polyethylene oxide, or combination thereof. In an embodiment, the solvent-removable pore building agent is 1,1,1-tris(hydroxymethyl)ethane.

Figure 1:
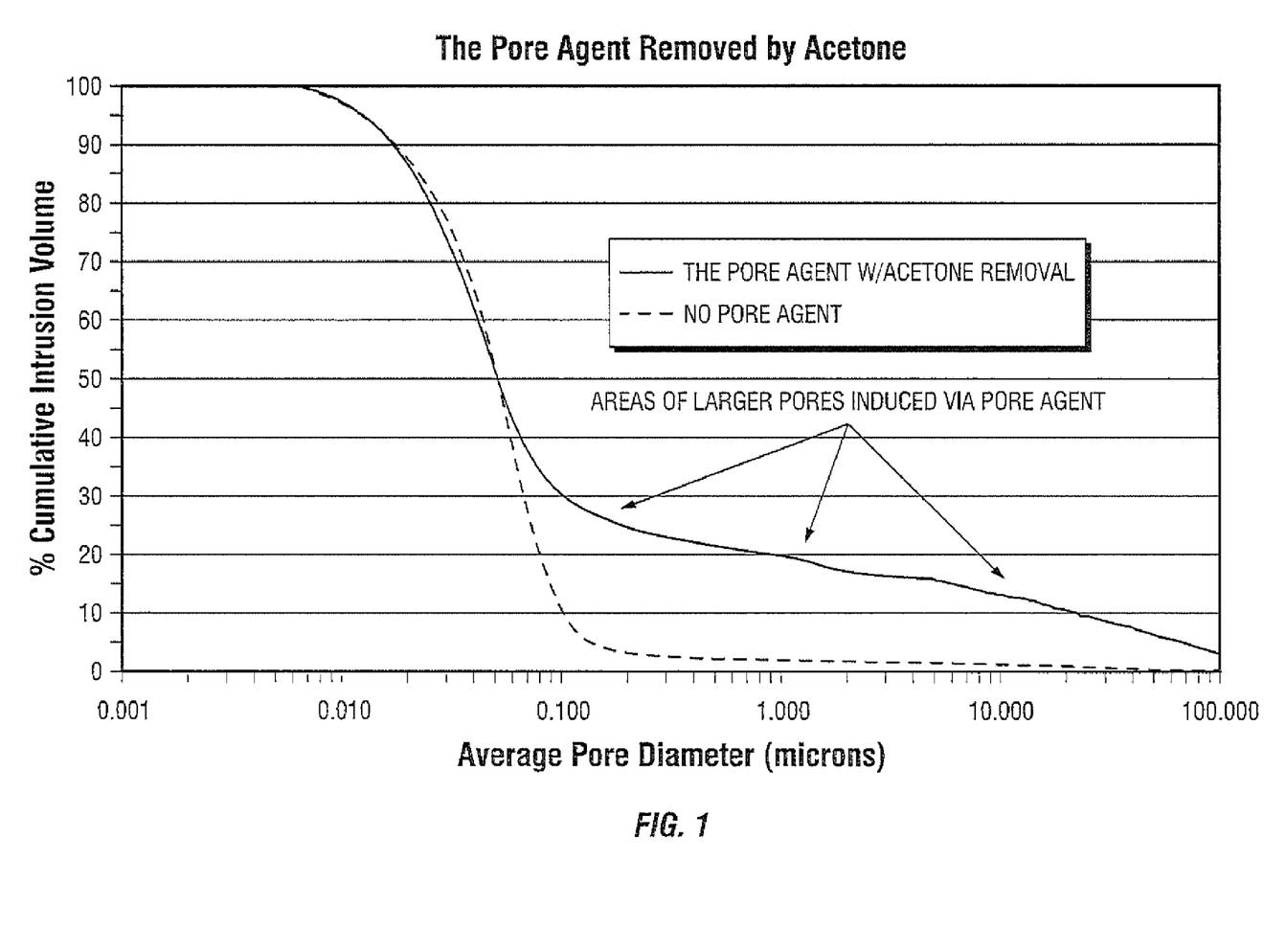
FIG. 1 illustrates percent cumulative intrusion volume against pore diameter for no pore agent and use of a pore agent.
Figure 2:
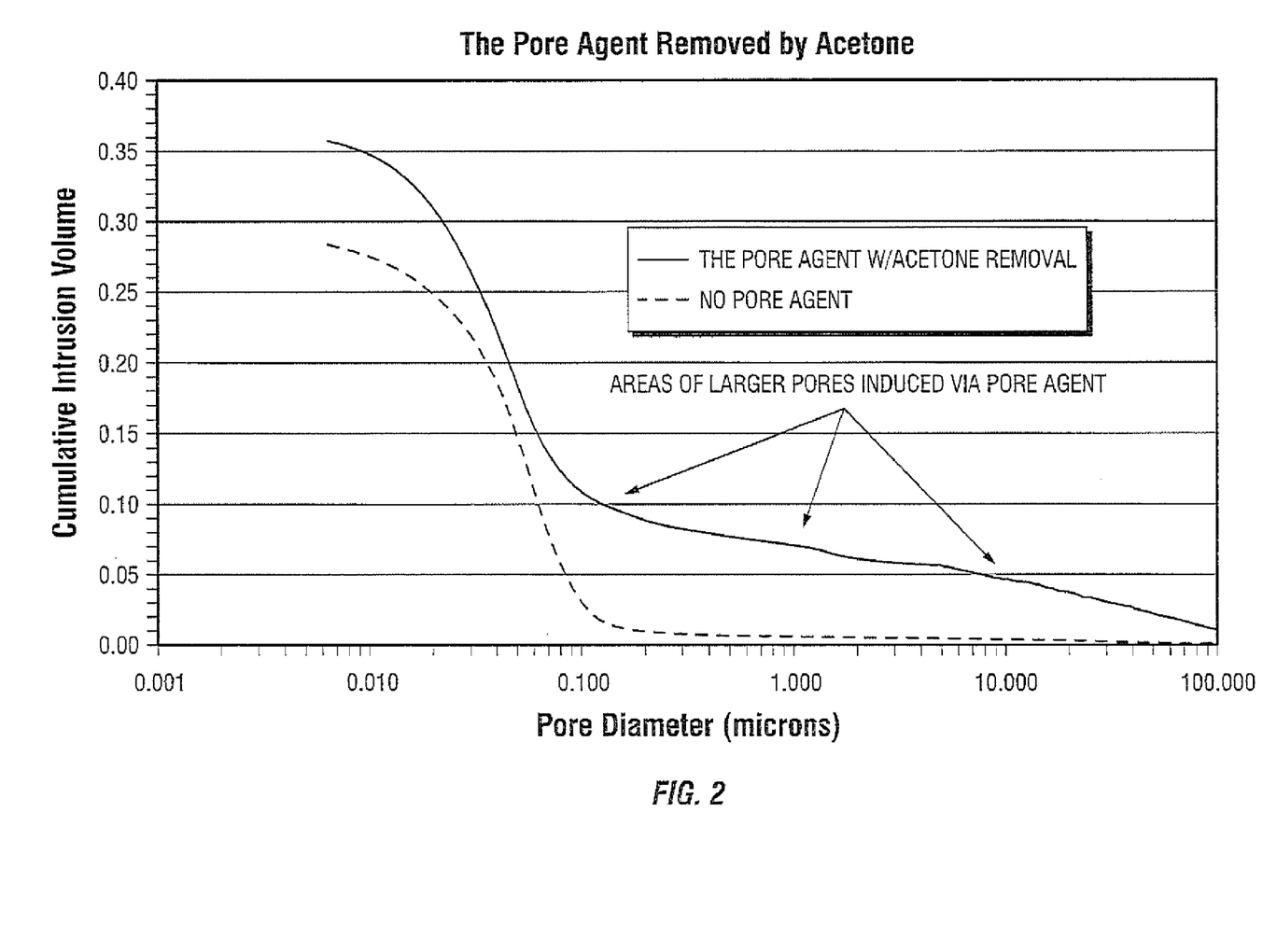
FIG. 2 illustrates cumulative intrusion volume against pore diameter for no pore agent and use of a pore agent.
Figure 3:
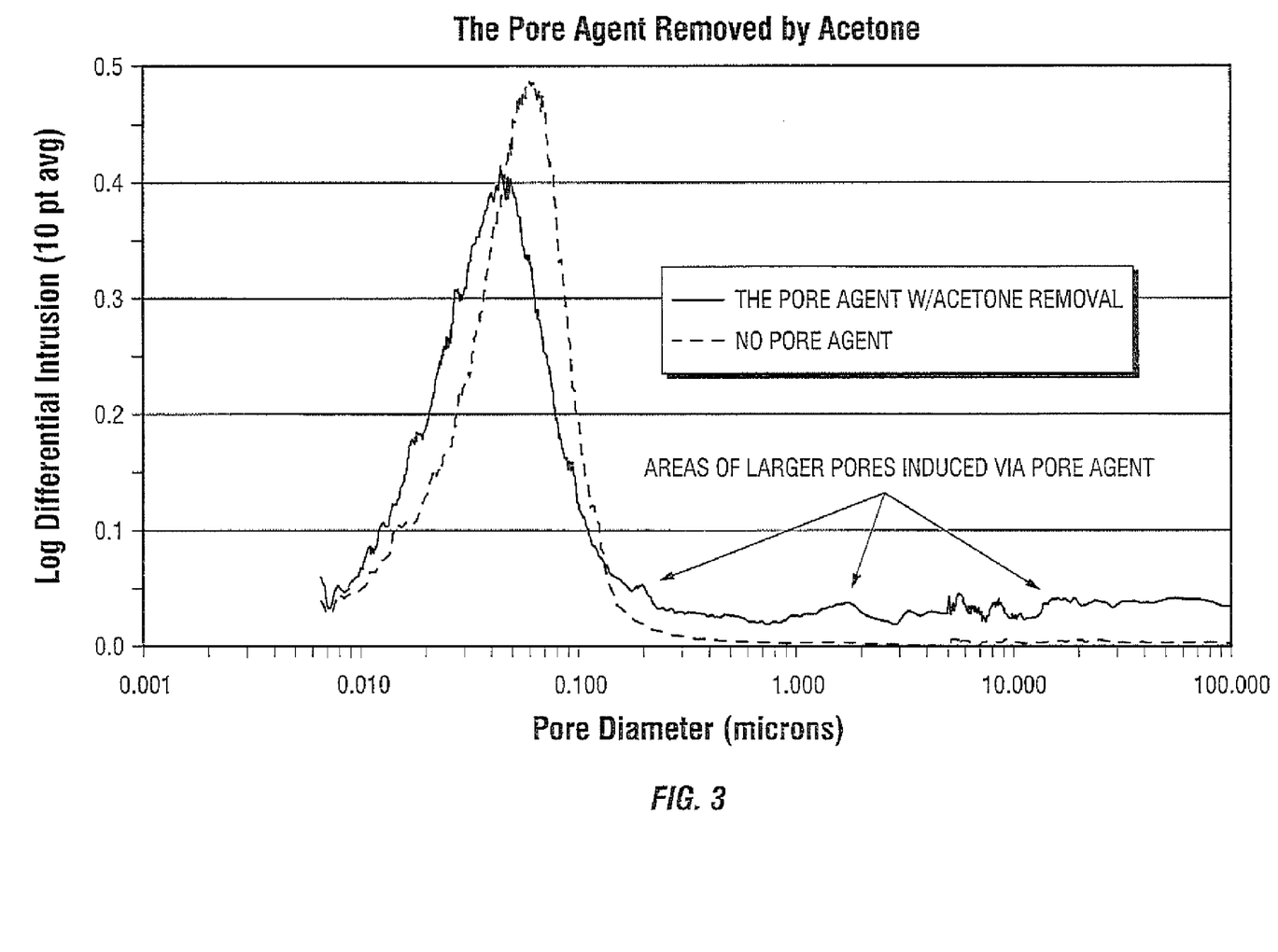
FIG. 3 illustrates log differential intrusion against pore diameter for no pore agent and use of a pore agent.

Addition of the solvent-removable pore building agent allows for rapid internal diffusion of product and reactant gases within the final shaped body catalyst. Without being limited by theory, the larger pores constitute flow arteries for distribution of these gases, thereby providing access for reaction gases to the active surfaces of the catalyst and egress of the product gases from finer pores of the catalyst. Further, without being limited by theory, this rapid exchange of gases allows for maximum effective use of more of the internal surface of the catalyst in the catalytic oxidation of $C_4$ hydrocarbons to maleic anhydride. The catalyst may therefore be formed into large tablets or pellets, resulting in low pressure drop through the catalyst bed without sacrificing productivity. FIGS. 1-3 illustrate the advantages of a pore building agent in relation to no pore building agent.

The catalysts may also exhibit crush strengths satisfactory for use in commercial reactors. Gravity and other compaction forces tend to crush porous catalyst bodies to a powder form, which may result in high pressure drop through the catalyst bed. Without being limited by theory, inadequate crush strength is generally associated with low apparent density of the catalyst bodies. Despite their high total pore volume and large proportion of macropores, the vanadium/phosphorous oxide catalysts have been found to exhibit a substantial normalized apparent shaped body density, in the range of between about 1.0 and about 2.0 $g/cm^3$ and a crush strength of at least about 4 pounds, alternatively at least about 6 pounds to about 10 pounds. It is to be understood that normalized apparent shaped body density is the same as measured apparent density where the solid phase of the catalyst is entirely constituted of vanadium/phosphorus oxide catalyst. Where the solid phase contains a foreign material, the normalized apparent density may be determined by adjusting the measured apparent density for the weight fraction of VPO in the catalyst body. Thus if:

$a_n$=the normalized apparent body density;
$a_m$=the measured apparent body density;
x=the weight fraction VPO in the catalyst body; then
$a_n = a_m x$ Where no foreign material is present, the normalized (and measured) apparent body density is between about 1.25 g/cm$^3$ and about 2.0 g/cm$^3$.

The granules and optional solvent-removable pore building agent mixture may then be compressed into a predetermined shape, such as pellets, tablets, spheres, cubes or other shaped body, in a press or die. The pellet or shaped body contains a structure of mixed particulate vanadium/phosphorus oxide structure and optional solvent-removable pore building agent having a principal dimension, of at least about ⅛ inch, at least about 5/32 inch to ½ inch and therefore a volume per shaped body catalyst of at least about 0.02 cm$^3$, preferably at least about 0.03 cm$^3$, more preferably at least about 0.05 cm$^3$.

In an embodiment, the solvent-removable pore building agent may be removed from the shaped body catalyst by applying the appropriate solvent to the shaped body catalyst. For example, the solvent-removable pore building agent may be removed from the catalyst such as by soaking and/or washing the catalyst at least once in the appropriate solvent for a certain period of time. The soaking period may depend on the particular solvent-removable pore building agent/solvent combination but may generally range from about 2 hours to about 24 hours, alternatively from about 6 hours to about 8 hours, and alternatively from about 6 hours to about 24 hours. The amount of solvent that may be used may range from about a 1:2 to 2:1 weight ratio of solvent to shaped body catalyst. The solvent-removable pore building agent may also be removed from the shaped body catalyst by washing the catalyst in a continuous stream of solvent. Again, the amount of washing may depend on the particular solvent-removable pore building agent/solvent combination.

Any solvent that may solubilize the solvent-removable pore building agent may be used. For example, the solvent may include one or more low molecular weight alcohols such as methanol or ethanol, a ketone such as acetone or methyl ethyl ketone, a supercritical $CO_2$, and/or esters such as ethyl acetate. For instance, an embodiment includes the solvent comprising ethanol, methanol, methyl ethyl ketone, ethyl acetate, acetone, supercritical $CO_2$ or combination thereof.

After the solvent-removable pore building agent is removed, no substantial residue of carbon, ash or adsorbed organic species may remain at the internal surfaces of the catalyst, which allows for the highest feasible catalyst activity. Furthermore, the solvent-removable pore building agent may be recovered from the solvent by any suitable means such as distillation or extraction.

The pellet or other shaped body catalyst may then be dried at a temperature range from about 45° C. to about 75° C. for a period of time ranging from about 1 hour to about 24 hours to produce the vanadium/phosphorus oxide catalyst.

The vanadium/phosphorus oxide catalysts prepared may be useful in a variety of reactors to convert non-aromatic hydrocarbons to maleic anhydride. The catalysts may be used in a fixed-bed reactor in the form of tablets, pellets or the like, or in a fluid-bed or transport-bed reactor using comminuted catalyst particles having a particle size of less than about 300 microns.

In one embodiment, the vanadium/phosphorus oxide catalysts are used in fixed-bed (tubular), heat exchanger-type reactors. The tubes of such reactors may be constructed of iron, stainless steel, carbon steel, nickel, and/or glass and may vary in diameter from about 0.635 cm (0.25 inch) to about 3.81 cm (1.5 inches) and in length from about 15.24 cm (6 inches) to about 609.6 cm (20 feet) or more. It is desirable to have the surfaces of the reactors at relatively constant temperatures, and some medium to conduct heat from the reactors. Without being limited by theory, such medium aids in temperature control. Nonlimiting examples of such media include Woods metal, molten sulfur, mercury, molten lead, and eutectic salt baths. A metal block reactor whereby the metal surrounding the tube acts as a temperature regulating body may also be used.

The reaction to convert non-aromatic hydrocarbons to maleic anhydride may include only contacting the hydrocarbons having at least four (4) carbons in a straight chain (or in a cyclic structure) admixed with a molecular oxygen-containing gas (including molecular oxygen), such as air or molecular oxygen-enriched air, with the vanadium/phosphorus oxide catalyst at elevated temperatures. In addition to the hydrocarbon and molecular oxygen, other gases such as nitrogen and steam may be present or added to the reactant feed stream. In an embodiment, the hydrocarbon may be admixed with the molecular oxygen-containing gas, preferably air, at a concentration of from about one (1) mole percent to about ten (10) mole percent hydrocarbon and contacted with the vanadium/phosphorus oxide catalyst at a space velocity of about 100 hr$^{-1}$ to about 4,000 hr$^{-1}$ at a temperature between about 300° C. and about 600° C., preferably 1,500 hr$^{-1}$ and about 325° C. to about 425° C., to provide an excellent yield and selectivity to maleic anhydride.

The reaction may be conducted at atmospheric, super atmospheric, or subatmospheric pressure. In an embodiment, the reaction may be conducted at or near atmospheric pressure. Generally, pressures of from about $1.013 \times 10^{-2}$ kPa-gauge (14.7 psig, 1 atmosphere) to about $3.45 \times 10^{-2}$ kPa-gauge (50 psig) may be conveniently employed.

A large number of nonaromatic hydrocarbons having from four to ten carbon atoms may be converted to maleic anhydride using the catalysts prepared by the process of the instant invention. In an embodiment, the hydrocarbon may contain not less than four carbon atoms in a straight chain or in a cyclic ring. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride using the shaped catalyst structures of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

Cyclic compounds such as cyclopentane and cyclopentene also are satisfactory feed materials for conversion to maleic anhydride using the vanadium/phosphorous oxide catalysts.

Of the aforementioned feedstocks, n-butane is the preferred saturated hydrocarbon, and the butenes are the preferred unsaturated hydrocarbons, with n-butane being most preferred of all feedstocks. It will be noted that the aforementioned feedstocks may not be pure substances but may be technical grade hydrocarbons.

In an embodiment, the principal product from the oxidation of the aforementioned suitable feedstock is maleic anhydride, although small amounts of citraconic anhydride (methyl maleic anhydride) may also be produced when the feedstock is a hydrocarbon containing more than four carbon atoms. The maleic anhydride produced by using the vanadium/phosphorus oxide catalysts may be recovered by any suitable means. For example, maleic anhydride may be recovered by direct condensation or by absorption in suitable media with subsequent separation and purification of the maleic anhydride.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

Example 1

A catalyst precursor was prepared in accordance with Example 1 of U.S. Pat. No. 5,137,860, which is incorporated by reference herein in its entirety. In a 12-liter, round bottom flask, fitted with a paddle stirrer, a thermometer, a heating mantle, and a reflux condenser, was charged 9,000 mL of isobutyl alcohol, 378.3 g (4.20 mol) of oxalic acid ($C_2H_2O_4$), and 848.4 g (4.66 mol) of vanadium pentoxide ($V_2O_5$). To this stirred mixture was added 997.6 g (10.76 mol) of phosphoric acid ($H_3PO_4$, 105.7% by weight). The resultant mixture was refluxed for about 16 hours to give a bright blue mixture. After stripping off approximately 25% (2.2 L) of the isobutyl alcohol over a 1-hour period, the mixture was cooled and approximately 50% of the remaining isobutyl alcohol removed by decantation. The resultant concentrated slurry was then quantitatively transferred to a flat porcelain dish and dried for 24 hours at 110°-150° C. in nitrogen. The dried material was thereafter heated in air at 250°-260° C. for approximately 5 hours to yield a grey-black catalyst precursor powder.

The catalyst precursor powder was blended to contain approximately three (3.0) weight % graphite and compressed on a Stokes 512 Rotary Tableting machine equipped with appropriate dies and punches to produce catalyst precursor cylindrical slugs having a ½ inch diameter, a 0.10-0.12 thickness, and a density of about 1.50 g/cm$^3$.

The catalyst precursor slugs were then activated in accordance as taught in U.S. Pat. No. 5,137,860. The catalyst precursor slugs were placed onto a 30.48 cm×30.48 cm×2.54 cm tray formed from stainless steel mesh screen having approximately 40% open area stainless steel, which was placed in a box oven. The slugs were then heated in the initial heat-up stage from room temperature (approximately 25° C.) to 275° C. in air with no control of the heat-up rate. The temperature was thereafter increased in the rapid heat-up stage to 425° C. at a programmed rate of 4° C./min in an atmosphere of 50 mol % air/50 mol % steam. The temperature was maintained at 425° C. in the maintenance/finishing stage, first in the rapid heat-up stage atmosphere for a period of 1 hour, and thereafter in an atmosphere of 50 mol % nitrogen/50 mol % steam for a period of 6 hours.

The activated catalyst was then granulated to pass through an 18 mesh screen, blended with stearic acid to produce a mixture containing 10% stearic acid by weight, and compressed to produce ¼ inch trilobe pellets having three equidistant grooves etched in the longitudinal surface. The stearic acid was then removed from the trilobe pellets by placing the pellets into a box oven purged with nitrogen gas and heating the pellets approximately 240° C. for one hour. The atmosphere in the oven was then changed to 50 volume percent nitrogen and 50 volume percent steam, and air was incremented in three steps over approximately 60 minutes to give a gas composition of [25:25:50] volume per cent [air:nitrogen:steam]. The temperature was maintained at 240° C. in this atmosphere for approximately 60 minutes.

The vanadium/phosphorus oxide catalyst pellets were performance tested at a standardized set of reaction conditions of 2.0±0.2 mol % n-butane in synthetic air (21 mol % oxygen/71 mol % helium), 1.034×10$^{-2}$ kPa-gauge (15.0 psig) inlet pressure, and 1,500 GHSV. The catalyst pellets (12.0 g) were charged to a 1.092 cm inside diameter×30.48 cm long (0.43 in. inside diameter×1 ft long) reactor to provide a catalyst bed of approximately 15.24 cm (6 in.) in length. The catalyst pellets were then run at 85±2 mol % n-butane conversion for about 100 hours and generated a maleic anhydride yield of 57.9%.

Comparative Example 1

A catalyst precursor powder was prepared according to the method described in EXAMPLE 1. The catalyst precursor powder was then blended to contain approximately ten (10) weight % stearic acid and compressed oil a Stokes 512 Rotary Tableting machine equipped with appropriate dies and punches to produce catalyst precursor slugs having a ½ inch diameter, a 0.10-0.12 thickness, and a density of about 1.30-1.40 g/cm$^3$. The slugs were then granulated to less than 1 mm particles, which were then tableted to produce ¼ inch trilobe pellets having three equidistant grooves etched in the longitudinal surface.

The stearic acid was then removed from the trilobe pellets by placing the pellets in a box oven purged with nitrogen gas and heating the pellets at approximately 240° C. for one hour. The atmosphere in the oven was then changed to 50 volume percent nitrogen and 50 volume percent steam, and air was incremented in three steps over approximately 60 minutes to give a gas composition of [25:25:50] volume per cent [air:nitrogen:steam]. The temperature was maintained at 240° C. in this atmosphere for approximately 60 minutes.

The ¼ inch trilobe pellets were then activated similar to the activation procedure of EXAMPLE 1. After cooling, the trilobe pellets were performance tested as described in EXAMPLE 1 and generated a maleic anhydride yield of 56.8%.

Example 2

A catalyst precursor powder was prepared according to the procedure described in EXAMPLE 1. The catalyst precursor powder was then blended to contain three (3) weight percent graphite and compressed on a Stokes 512 Rotary Tableting machine to produce catalyst precursor cylindrical slugs having a ½ inch diameter, a 0.10-0.12 thickness, and a density of about 1.50 g/cm$^3$.

The catalyst precursor slugs were activated by the heat treatment described in EXAMPLE 1. The activated catalyst was then granulated to pass through an 18 mesh screen and then blended with 1,1,1-tris(hydroxymethlylethane) to provide a mixture containing ten (10) weight percent 1,1,1-tris (hydroxymethlylethane). This mixture was then compressed to produce ¼ inch diameter trilobe pellets. The 1,1,1-tris (hydroxymethylethane) was then removed from the trilobe pellets by submersing the pellets in an acetone bath for 22.5 hours at a 1:1.5 pellet to acetone ratio. The pellets were removed, further washed with acetone, and then dried at 60° C. for 18 hours.

The trilobe pellets were then performance tested according to the method described in EXAMPLE 1 and generated a maleic anhydride yield of 61.9%.

Comparative Example 2

A catalyst precursor powder was prepared according to the method described in EXAMPLE 1. The catalyst precursor powder was then blended to contain approximately ten (10) weight percent 1,1,1-tris(hydroxymethylethane) and compressed on a Stokes 512 Rotary Tableting machine equipped with appropriate dies and punches to produce catalyst precursor slugs having a ½ inch diameter, a 0.10-0.12 thickness, and a density of about 1.30-1.40 g/cm$^3$. The slugs were then granulated to less than 1 mm particles which were then tableted to produce ¼ inch trilobe pellets having three equidistant grooves etched in the longitudinal surface.

The 1,1,1-tris(hydroxymethylethane) was then removed from the trilobe pellets by placing the pellets in acetone for 22.5 hours at a 1:1.5 pellet to acetone ratio. The pellets were then removed, further washed with acetone, then dried at 60° C. for 18 hours.

The trilobe pellets were then activated similar to the activation procedure of EXAMPLE 1. After cooling, the trilobe pellets were performance tested as described in EXAMPLE 1 and generated a maleic anhydride yield of 58.8%.

From the results above, it can be seen that activating the catalyst precursor slug prior to tableting improves the performance of the vanadium/phosphorus oxide catalyst. The catalyst's performance may be further improved by treating the activated catalyst precursor slug with a solvent-removable pore building agent prior to tableting. It is believed that activating the catalyst precursor slug, which is less dense than the tablet, prior to tableting allows the slug to be uniformly gas and thermally treated and subsequently provides a vanadium/phosphorus oxide catalyst exhibiting uniform chemical properties, and thus, improved selectivity.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A process for the preparation of a vanadium/phosphorus oxide catalyst comprising:
   (a) preparing a catalyst precursor powder by mixing a vanadium compound with a phosphorus compound in a medium comprising alcohol and drying the mixture;
   (b) forming the catalyst precursor powder into catalyst precursor slugs under compression;
   (c) converting the catalyst precursor slugs into an activated catalyst by heating the catalyst precursor slugs in three controlled stages;
   (d) forming the activated catalyst into a predetermined shape under compression to produce the vanadium/phosphorus oxide catalyst; and
   (e) treating the activated catalyst with a solvent.

2. The process of claim 1, wherein prior to step (d), the activated catalyst is granulated and then mixed with a solvent-removable pore building agent in proportions sufficient to provide a pore building agent concentration of between about 6% and about 16% by weight based on the total weight of the activated catalyst.

3. The process of claim 2, wherein the treating the activated catalyst with a solvent comprises removing the solvent-removable pore building agent.

4. The process of claim 3, wherein the solvent-removable pore building agent is trimethylolpropane, maleic anhydride, polyethylene oxide, 1,1,1-tris(hydroxymethyl)ethane, or combination thereof.

5. The process of claim 3, wherein the solvent-removable pore building agent is 1,1,1-tris(hydroxymethyl)ethane.

6. The process of claim 3, wherein the solvent comprises ethanol, methanol, methyl ethyl ketone, ethyl acetate, acetone, supercritical $CO_2$, or combination thereof.

7. The process of claim 1, wherein the predetermined shape is a pellet.

8. A process for the oxidation of a hydrocarbon comprising: contacting a hydrocarbon with a vanadium/phosphorus oxide catalyst at a temperature between about 300° C. and about 600° C., wherein the vanadium/phosphorus oxide catalyst is prepared by converting catalyst precursor slugs comprising vanadium and phosphorus and optional promoter elements into an activated catalyst in three controlled stages; granulating the activated catalyst to produce granules; treating the granules with a solvent; and shaping the granules into a predetermined shape thereby forming the vanadium/phosphorus oxide catalyst.

9. The process of claim 8, wherein a solvent-removable pore building agent is mixed with the granules.

10. The process of claim 8, wherein the hydrocarbon is a hydrocarbon having four carbons in a straight chain.

11. The process of claim 8, wherein the hydrocarbon is n-butane.

12. The process of claim 9, wherein the solvent-removable pore building agent is removed by treating the granules with the solvent.

* * * * *